United States Patent [19]

Hirai et al.

[11] Patent Number: 5,756,675
[45] Date of Patent: May 26, 1998

[54] IL-1α DERIVATIVES

[75] Inventors: Yoshikatsu Hirai; Satoru Nakai, both of Tokushima-ken; Koutoku Aihara, Tokushima; Kazuyoshi Kawai; Mayumi Kaneta, both of Tokushima-ken; Takashi Kamogashira, Tokushima; Yoshihiro Masui, Tokushima-ken, all of Japan

[73] Assignee: Otsuka Pharmaceutical Co., Ltd., Tokyo-To, Japan

[21] Appl. No.: 254,419

[22] Filed: Jun. 6, 1994

Related U.S. Application Data

[60] Continuation of Ser. No. 808,678, Dec. 17, 1991, abandoned, which is a division of Ser. No. 386,073, Jul. 28, 1989, Pat. No. 5,120,534.

[30] Foreign Application Priority Data

Jul. 29, 1988 [JP] Japan ................... 63-191009
Aug. 4, 1988 [JP] Japan ................... 63-195419

[51] Int. Cl.⁶ .................................... C07K 14/54
[52] U.S. Cl. ................ 530/351; 530/350; 435/69.52
[58] Field of Search .................... 530/351, 350; 435/69.52; 930/141

[56] References Cited

U.S. PATENT DOCUMENTS

| | | | |
|---|---|---|---|
| 5,008,374 | 4/1991 | Nakai et al. | 530/351 |
| 5,017,692 | 5/1991 | Zurawski et al. | 530/351 |
| 5,047,505 | 9/1991 | Huang | 530/351 |
| 5,093,242 | 3/1992 | Bachman et al. | 435/647 |

FOREIGN PATENT DOCUMENTS

| | | |
|---|---|---|
| 0188864 | 7/1986 | European Pat. Off. |
| 0188920 | 7/1986 | European Pat. Off. |
| 188920A | 8/1986 | European Pat. Off. |
| 0200986 | 11/1986 | European Pat. Off. |
| 0237073 | 9/1987 | European Pat. Off. |
| 0259160 | 3/1988 | European Pat. Off. |
| 0324447 | 7/1989 | European Pat. Off. |
| 62-185097 | 8/1987 | Japan. |
| 62-246522 | 10/1987 | Japan. |
| 1137977 | 5/1989 | Japan. |
| 2009899 | 1/1990 | Japan. |
| 2186580 | 7/1987 | United Kingdom. |
| WO 88/00969 | 2/1988 | WIPO. |

OTHER PUBLICATIONS

Wells. Biochemistry 29:8509–8517, Sep. 1990.
Bowie et al. Science, 247 1990, pp. 1306–1310.
Masley et al, PNAS 84, 1987, pp. 4572–4576.
Wingfield et al, Prot. Engineering 1(5) 1987, pp. 413–417.
Gronenborn et al. FEBS 231(1) 1988, pp. 135–138.
Mac Donald et al, FEBS 209(2) 1986, pp. 295–298.
Daumy et al Brochem Biophys Oct. 1989, pp. 32–42, vol. 998.
Zucali et al, Exp Hematul. 18, 1990, pp. 1078–1082.

Primary Examiner—Elizabeth C. Kemmerer
Attorney, Agent, or Firm—Sughrue, Mion, Zinn, Macpeak & Seas, PLLC

[57] ABSTRACT

The present invention provides a medicament for treating thrombocytopenia comprising as an active component at least one polypeptide selected from IL-1 and derivative thereof and a Il-1α derivative having an amino acid sequence of the formula (α) which is so modified as to fulfill at least one of the requirements of: deletion of the 16-position Arg; replacement of the 16-position Arg by another amino acid residue; deletion of the sequence of the 1-position Ser to the 14-position Phe and deletion of the amino acid sequence of the 1-position Ser to the 15-position Met.

2 Claims, 2 Drawing Sheets

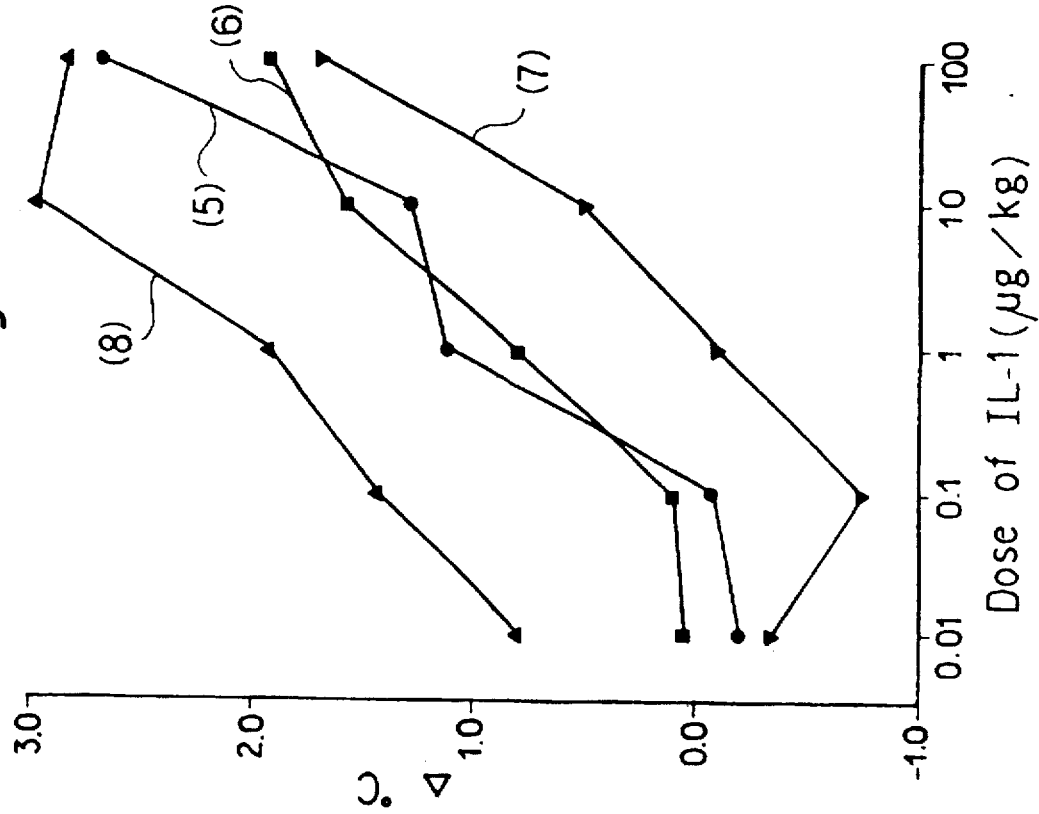
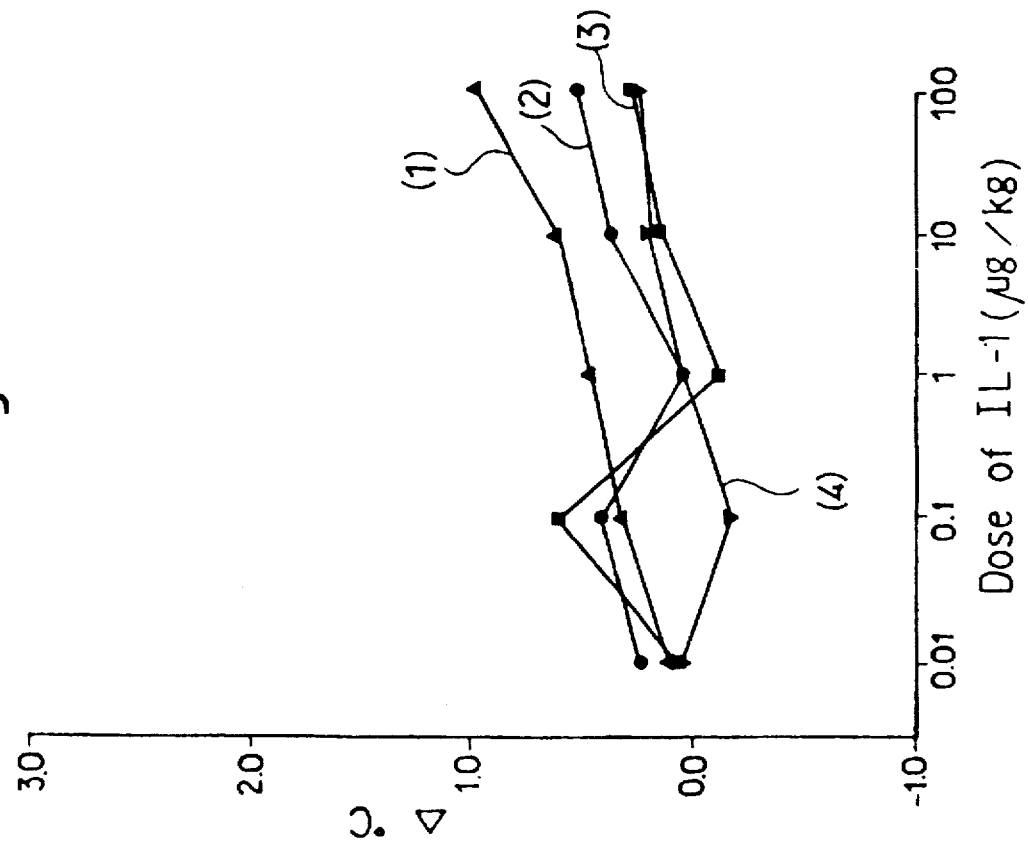
Figure 2A
Figure 2B

IL-1α DERIVATIVES

This is a Continuation of application Ser. No. 07/808,678 filed 17 Dec. 1991, now abandoned which is a divisional of application Ser. No. 07/386,073 filed 28 Jul. 1989, now U.S. Pat. No. 51,20,534.

The present invention relates to a medicament for treating thrombocytopenia, and more particularly to a medicament comprising as an active component at least one selected from interleukin-1 (IL-1) and derivatives thereof and to novel IL-1α derivatives useful as an active component of said medicament.

BACKGROUND OF THE INVENTION

The technology of cancer therapy has been advanced in recent years. Remarkable advances have been made not only in conventional surgical operations but also in chemotherapy, radiotherapy and immunotherapy. However, the advantages of chemotherapy and radiotherapy in particular are liable to be accompanied by severe side effects.

The ideal chemotherapeutic agent is such that it displays a carcinostatic effect but little or no adverse affect on normal tissues. However, since conventional chemotherapeutic agents induce strong inhibition of the bone marrow accompanied by decreases in leukocytes and platelets, it is impossible to administer them consecutively over a long period, and the medication must be interrupted due to these side effects. The irradiation of X-ray or γ-ray for radiotherapy likewise causes adverse effects on hematogenic tissues such as the bone marrow. Particularly if leukocytes, platelets, etc. are markedly decreased, the irradiation should be discontinued.

Transfusion is one of the conventional methods of inhibiting or ameliorating reductions in platelets, etc. which serve as dose-limiting factors. However, since blood cells such as platelets and leucocytes have a short life, fresh blood cells should be frequently replenished with. When bone marrow disorder is severe, bone marrow transplantation should be performed. Such bone marrow transplantation is intended to transfer hematogenic stem cells of the bone marrow to the body and thus to produce platelets in the body. This method has afforded an epochal effect in therapy for certain types of tumors and thus established a fundamental therapy for malignant tumors. However, the above bone marrow transplantation has problems as follows:

It is very difficult to supply donors of bone marrow fitting to patients. Even if a donor is supplied, the transplantation operation is difficult and it generally takes several weeks for the bone marrow transplanted to take, commence hematogenesis and then produce leukocytes, platelets, etc. in peripheral blood. During this period, the patient therefore may hover between life and death.

As described above, although transfusion and bone marrow transplantation are methods for ameliorating decreases in platelets and like side effects which occur in chemotherapy, radiotherapy or like therapy for cancer, bone marrow transplantation has various problems. In order to overcome such problems, patients themselves should have an improved hematogenic function. Therefore it is desired in the pharmaceutical field to develop a novel medicament having activity to promote hematogenesis. Particularly a medicament having activity to promote production of platelets is totally unknown.

SUMMARY OF THE INVENTION

An object of the present invention is to provide a novel medicament for alleviating symptoms such as thrombocytopenia, etc. to fill the demand described above.

Another object of the invention is to provide a IL-1 derivative, especially a IL-1α derivative, useful as an active component of the medicament for treating thrombocytopenia.

DETAILED DESCRIPTION OF THE DRAWINGS

Figure 1:
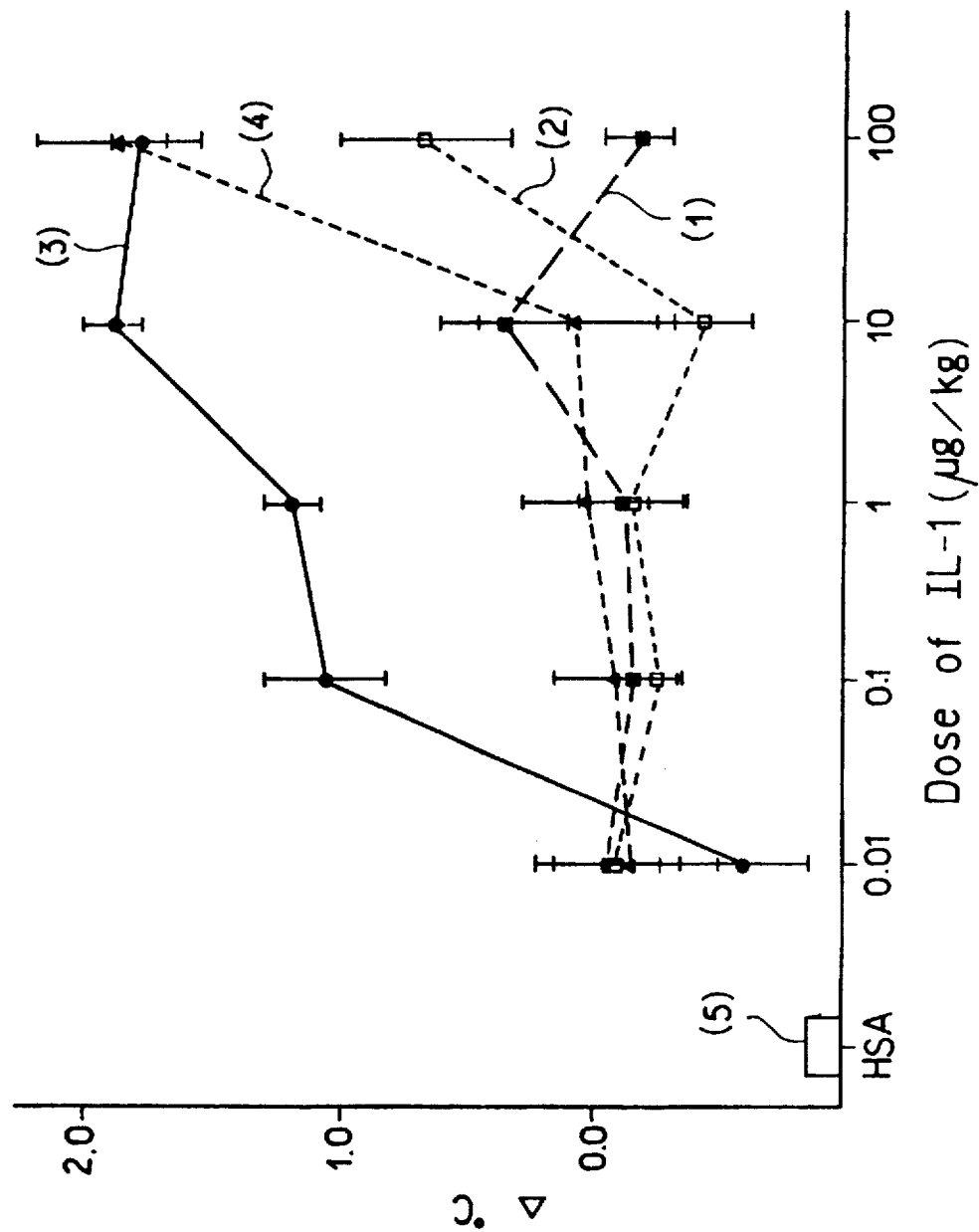

FIGS. 1, and 2A and 2B depict the results of the inhibition of pyrogenicity with both species of IL-1 and various derivatives thereof. The numerical line designations represent the different IL-1 species tested.

DETAILED DESCRIPTION OF THE INVENTION

The above object is accomplished by a medicament for treating thrombocytopenia which contains at least one polypeptide from IL-1 and IL-1 derivatives.

The inventors conducted extensive research in view of the above situation and found that IL-1 and IL-1 derivatives, which were previously proved to have various physiological effects including the effect to activate lymphocytes and the effect to promote producing interleukin-2 (IL-2), antibodies, etc. and the novel IL-1 derivatives developed by the inventors have surprisingly remarkable effect to inhibit reduction in platelets (effect to increase platelets) and are very useful as medicaments for thrombocytopenia to attain the above object. The invention was achieved based on these findings.

The medicament for treating thrombocytopenia of the invention, which comprises IL-1 or its derivative as an active component, displays a remarkable effect to increase platelets and is therefore very useful for the therapy of thrombocytopenia.

IL-1's which are active components for use in the present invention include IL-1α having a sequence 159 amino acids and IL-1β having a sequence 153 amino acids (Proc. Natl. Acad. Sci., 81, 7907–7911 (1984); Nature, 315, 641 (1985); Nucleic Acid Research, 13(16), 5869 (1985)). The sequence of amino acids is identified from the base sequence of gene coding for the polypeptide having LAF (lymphocyte activating factor) activity. These interleukins may be native interleukins isolated in a conventional manner from cells which produce them or recombinant interleukins prepared by gene engineering techniques.

The primary amino acid sequence of the native IL-1α is represented by the following formula (A):

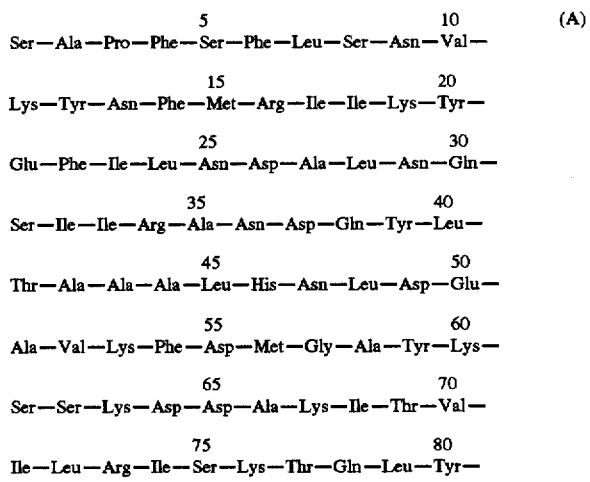

(A)

```
              5                    10
Ser—Ala—Pro—Phe—Ser—Phe—Leu—Ser—Asn—Val—

15                   20
Lys—Tyr—Asn—Phe—Met—Arg—Ile—Ile—Lys—Tyr—

25                   30
Glu—Phe—Ile—Leu—Asn—Asp—Ala—Leu—Asn—Gln—

35                   40
Ser—Ile—Ile—Arg—Ala—Asn—Asp—Gln—Tyr—Leu—

45                   50
Thr—Ala—Ala—Ala—Leu—His—Asn—Leu—Asp—Glu—

55                   60
Ala—Val—Lys—Phe—Asp—Met—Gly—Ala—Tyr—Lys—

65                   70
Ser—Ser—Lys—Asp—Asp—Ala—Lys—Ile—Thr—Val—

75                   80
Ile—Leu—Arg—Ile—Ser—Lys—Thr—Gln—Leu—Tyr—
```

-continued

```
              85                      90
Val—Thr—Ala—Gln—Asp—Glu—Asp—Gln—Pro—Val—

95                     100
Leu—Leu—Lys—Glu—Met—Pro—Glu—Ile—Pro—Lys—

105                     110
Thr—Ile—Thr—Gly—Ser—Glu—Thr—Asn—Leu—Leu—

115                     120
Phe—Phe—Trp—Glu—Thr—His—Gly—Thr—Lys—Asn—

125                     130
Tyr—Phe—Thr—Ser—Val—Ala—His—Pro—Asn—Leu—

135                     140
Phe—Ile—Ala—Thr—Lys—Gln—Asp—Tyr—Trp—Val—

145                     150
Cys—Leu—Ala—Gly—Gly—Pro—Pro—Ser—Ile—Thr—

155
Asp—Phe—Gln—Ile—Leu—Glu—Asn—Gln—Ala
```

The primary amino acid sequence of the native IL-1β is represented by the following formula (B).

```
              5                      10              (B)
Ala—Pro—Val—Arg—Ser—Leu—Asn—Cys—Thr—Leu—

15                      20
Arg—Asp—Ser—Gln—Gln—Lys—Ser—Leu—Val—Met—

25                      30
Ser—Gly—Pro—Tyr—Glu—Leu—Lys—Ala—Leu—His—

35                      40
Leu—Gln—Gly—Gln—Asp—Met—Glu—Gln—Gln—Val—

45                      50
Val—Phe—Ser—Met—Ser—Phe—Val—Gln—Gly—Glu—

55                      60
Glu—Ser—Asn—Asp—Lys—Ile—Pro—Val—Ala—Leu—

65                      70
Gly—Leu—Lys—Glu—Lys—Asn—Leu—Tyr—Leu—Ser—

75                      80
Cys—Val—Leu—Lys—Asp—Asp—Lys—Pro—Thr—Leu—

85                      90
Gln—Leu—Glu—Ser—Val—Asp—Pro—Lys—Asn—Tyr—

95                     100
Pro—Lys—Lys—Lys—Met—Glu—Lys—Arg—Phe—Val—

105                     110
Phe—Asn—Lys—Ile—Glu—Ile—Asn—Asn—Lys—Leu—

115                     120
Glu—Phe—Glu—Ser—Ala—Gln—Phe—Pro—Asn—Trp—

125                     130
Tyr—Ile—Ser—Thr—Ser—Gln—Ala—Glu—Asn—Met—

135                     140
Pro—Val—Phe—Leu—Gly—Gly—Thr—Lys—Gly—Gly—

145                     150
Gln—Asp—Ile—Thr—Asp—Phe—Thr—Met—Gln—Phe—

Val—Ser—Ser                                          (B)
```

The IL-1 derivatives include various derivatives. Typical examples of such IL-1 derivatives are the IL-1α and IL-1β derivatives having various amino acid sequences, which were disclosed in the prior applications by the present applicant (European Patent Publication Nos. 187991, 237967 and 237073).

The above IL-1α derivative has the amino acid sequence of the formula (A) which is modified so that at least one of Asn at the 36 position and Cys at the 141 position is deleted or replaced by another amino acid residue.

The IL-1β derivative has the modified amino acid sequence fulfilling at least one of the following requirements a) to d) in the amino acid sequence represented by the formula (B):

a) At least one amino acid residue selected from the group consisting Ala at the 1-position, Val at the 3-position, Arg at the 4-position, Ser at the 5-position, Cys at the 8-position, Arg at the 11-position, His at the 30-position, Cys at the 71-position, Lys at the 93-position, Lys at the 97-position, Arg at the 98-position, Phe at the 99-position, Lys at the 103-position, Trp at the 120-position, Tyr at the 121-position and Ser at the 153-position is deleted or replaced by another amino acid residue.

b) The amino acid sequence of Ala at the 1-position to Thr at the 9-position or at least one amino acid residue in this sequence is deleted (except that at least one amino acid residue selected from the group consisting of Ala at the 1-position, Val at the 3-position, Arg at the 4-position, Ser at the 5-position and Cys at the 8-position is deleted as stated in the requirement a)).

c) The amino acid sequence of Lys at the 103 position to Ser at the 153-position or at least one amino acid residue in this sequence is deleted (except that at least one amino acid residue selected from the group consisting of Lys at the 103-position, Trp at the 120-position, Tyr at the 121-position and Ser at the 153-position is deleted as stated in the requirement a)).

d) An amino acid residue, or the amino acid sequence of Met at the 1'-position to Asp at the 116'-position represented by the following formula (B'), or a portion of said sequence oriented to the C terminal is attached to the N terminal of the formula (B). Formula (B'):

```
              5'                     10'
Met—Ala—Glu—Val—Pro—Glu—Leu—Ala—Ser—Glu—

15'                     20'
Met—Met—Ala—Tyr—Tyr—Ser—Gly—Asn—Glu—Asp—

25'                     30'
Asp—Leu—Phe—Phe—Glu—Ala—Asp—Gly—Pro—Lys—

35'                     40'
Gln—Met—Lys—Cys—Ser—Phe—Gln—Asp—Leu—Asp—

45'                     50'
Leu—Cys—Pro—Leu—Asp—Gly—Gly—Ile—Gln—Leu—

55'                     60'
Arg—Ile—Ser—Asp—His—His—Tyr—Ser—Lys—Gly—

65'                     70'
Phe—Arg—Gln—Ala—Ala—Ser—Val—Val—Val—Ala—

75'                     80'
Met—Asp—Lys—Leu—Arg—Lys—Met—Leu—Val—Pro—

85'                     90'
Cys—Pro—Gln—Thr—Phe—Gln—Glu—Asn—Asp—Leu—

95'                    100'
Ser—Thr—Phe—Phe—Pro—Phe—Ile—Phe—Glu—Glu—

105'                    110'
Glu—Pro—Ile—Phe—Phe—Asp—Thr—Trp—Asp—Asn—

115'
Glu—Ala—Tyr—Val—His—Asp
```

Amino acids and polypeptides are herein referred to by abbreviations according to the nomenclature or rules recommended by IUPAC and IUPAC-IUB or by abbreviations conventionally used in the art. The nucleic acids in the base sequences are also similarly expressed.

The amino acid numbers or positions are given based on the amino acid sequences of the formula (A) (IL-1α) and formula (B) (IL-1β), unless otherwise stated, even in the case where there is a deletion or attachment. However, the number with a prime (') representing the position of an amino acid residue in the IL-1β derivative is given based on the amino acid sequence of the formula (B').

The amino acid residue to be attached to or substituted with a particular amino acid residue at a particular position in an amino acid sequence of the IL-1 derivative may be any of α-amino acid residues constituting human proteins. Particularly neutral amino acid residues are preferable. However, Cys is likely to form a disulfide linkage intra- or inter-molecularly with its SH group. In view of this, the desirable amino acid residues are those other than Cys.

In case of the IL-1α derivative, examples of more preferable α-amino acid residues constituting human protein are Asp for replacing Asn at the 36-position and Ser for replacing Cys at 141-position.

In case of the IL-1β derivative, examples of more preferable amino acid residues are Gly, Lys, Gln or Asp for replacing Arg at the 4-position; Ser or Ala for the 8-position Cys; Gln for the 11-position Arg; Tyr for the 30-position His; Ser, Ala or Val for the 71-position Cys; Leu or Asp for the 93-position Lys; Leu for the 98-position Arg; Gln for the 103-position Lys; Arg for the 120-position Trp; and Gln for the 121-position Tyr; Met, Leu, Arg or Asp for attaching to the N terminal.

The inventors succeeded in providing a novel IL-1α derivative useful as an active component of the inventive medicament for treating thrombocytopenia. This IL-1α derivative has features as follows.

More specifically, said IL-1α derivative has an amino acid sequence represented by the following formula Formula (α):

```
                              5                              10
Ser—Ala—Pro—Phe—Ser—Phe—Leu—Ser—Asn—Val—
                             15
Lys—Tyr—Asn—Phe—Met—Arg—Ile—Ile—Lys—Tyr—
                             25                              30
Glu—Phe—Ile—Leu—Asn—Asp—Ala—Leu—Asn—Gln—
                             35                              40
Ser—Ile—Ile—Arg—Ala—X—Asp—Gln—Tyr—Leu—
                             45                              50
Thr—Ala—Ala—Ala—Leu—His—Asn—Leu—Asp—Glu—
                             55                              60
Ala—Val—Lys—Phe—Asp—Met—Gly—Ala—Tyr—Lys—
                             65                              70
Ser—Ser—Lys—Asp—Asp—Ala—Lys—Ile—Thr—Val—
                             75                              80
Ile—Leu—Arg—Ile—Ser—Lys—Thr—Gln—Leu—Tyr—
                             85                              95
Val—Thr—Ala—Gln—Asp—Glu—Asp—Gln—Pro—Val—
                             95                             100
Leu—Leu—Lys—Glu—Met—Pro—Glu—Ile—Pro—Lys—
                            105                             110
Thr—Ile—Thr—Gly—Ser—Glu—Thr—Asn—Leu—Leu—
                            115                             120
Phe—Phe—Trp—Glu—Thr—His—Gly—Thr—Lys—Asn—
                            125                             130
Tyr—Phe—Thr—Ser—Val—Ala—His—Pro—Asn—Leu—
                            135                             140
Phe—Ile—Ala—Thr—Lys—Gln—Asp—Tyr—Trp—Val—
                            145                             150
YY—Leu—Ala—Gly—Gly—Pro—Pro—Ser—Ile—Thr—
                            155
Asp—Phe—Gln—Ile—Leu—Glu—Asn—Gln—Ala
``` wherein X and Y are α-amino acid residues constituting human proteins and which is so modified as to fulfill at least one of the requirements of: deletion of the 16-position Arg; replacement of the 16-position Arg by another amino acid residue; deletion of the amino acid sequence of Ser at the 1-position to Phe at the 14-position; and deletion of the amino acid sequence of Ser at 1-position to Met at 15-position.

In the formula (α), Asp is exemplified as a more preferable amino acid residue represented by X at the 36-position, and Ser is exemplified as a more preferable amino acid residue represented by Y at the 141-position. Gly is exemplified as a more preferable α-amino acid residue constituting human protein for replacing the 16position Arg.

Therefore, the present invention provides a IL-1α derivative having the above-modified amino acid sequence.

The IL-1α derivatives of the invention have platelet-increasing effect (hematogenic effect) and useful as a medicament for treating thrombocytopenia. Said IL-1α derivatives also have, similarly to conventional IL-1 derivatives, for example, physiological activity such as LAF activity, activity to inhibit growth of tumor cells (GIF activity), activity to promote production of various cytokines such as colony stimulating factor (CSF), interferon (IFN), interleukin-2 (IL-2) and interleukin-3 (IL-3), anti-inflammatory activity and activity to prevent radiation injury, and accordingly useful as immuno system stimulants, for example, for promoting production of antibodies and enhancing the effect of vaccines, antitumor agents, agents for promoting production of cytokines such as CSF, IFN, IL-2 and IL-3, anti-inflammatory agents, agents for preventing radiation disorders and other like medicinal agents. While fever may be caused as a side effect by conventional IL-1 derivatives, the IL-1α derivatives of the invention scarcely cause such fever and are low in toxicity.

The IL-1α derivative of the present invention can be prepared, for example, by gene engineering techniques using a gene coding for the specific polypeptide, i.e., by incorporating the gene into a microorganism vector to effect replication, transcription and translation within the cell of the microorganism to afford the desired derivative. This process is advantageous in that it is amenable to mass production.

Although the gene to be used in this process can be totally synthesized by chemical synthesis of nucleic acids by a usual method, for example, by the phosphite triester method (Nature, 310, 105 (1984)) or the like, it is convenient to utilize the gene coding for IL-1 or a precursor thereof. By a conventional method involving the above chemical synthesis, the gene is modified to a sequence of nucleic acids coding for the foregoing specific amino acid sequence, whereby the desired gene can be prepared easily.

The gene coding for IL-1 or a precursor thereof is already known (see Japanese Unexamined Patent Application No. 174022/1987).

The above-mentioned modified sequence of nucleic acids (bases) is prepared also by a known procedure, which executed according to the amino acid sequence of the desired polypeptide (see Molecular Cloning Cold Spring Harbor Laboratory (1982)).

For example, cleavage, ligation, phosphorylation, etc. of DNA can be carried out by usual methods including treatment with enzymes such as restriction enzymes, DNA ligase, polynucleotidekinase and DNA polymerase, which are readily available as commercial products. The isolation and purification of the gene and nucleic acids included in these methods are conducted also in the usual manner, for example, by agarose gel electrophoresis. As will be described partially later, the gene obtained is replicated using a usual vector. The DNA fragment coding for the desired amino acid sequence and synthetic linkers can be prepared also easily by the above-mentioned chemical synthesis. The codon corresponding to the desired amino acid and to be used in the above methods is known and is selected as desired. A usual method may be used for this purpose, for example, in view of the frequency of use of the codon of the host to be used (Nucl. Acids Res., 9, 43–73 (1981)). Further for the modification of the codon in the nucleic acid sequence concerned, for example, site-specific mutagenesis (Proc. Natl. Acad. Sci., 81, 5662–5666 (1984)) can be resorted to as usually done which employs a primer comprising a synthetic oligonucleotide of about 15–30 mer coding for the desired modified sequence.

The desired gene obtained by the foregoing process can be checked for its base sequence, for example, by the Maxam-Gilbert chemical modification method (Meth. Enzym., 65, 499–560 (1980)) or by the dideoxynucleotide chain termination method using M13 Phage (Messing, J. and Vieira, J., Gene, 19, 269–276 (1982)).

While the above process and procedures therefor will be described in the preparation examples to follow, the process is not specifically limited; any process already known in the art may be used.

The desired gene coding for a polypeptide having the above-specified amino acid sequence of the formula ($\alpha$) is thus provided. (The gene will hereinafter be referred to as the "present gene.")

The polypeptide of the present invention can be prepared by usual known gene recombination techniques using the present gene. More specifically, it is produced by preparing a recombinant DNA which can express the present gene in host cells, transforming the DNA into the host cell and incubating the transformant.

Useful host cells can be either eucaryotic or procaryotic cells. The eucaryotic cells include cells of vertebrate animals, yeasts, etc. Generally used as cells of vertebrate animals are, for example, COS cells which are cells of monkey (Y. Gluzman, Cell, 23, 175–182 (1981)), dihydrofolate reductase defective strain of Chinese hamster ovary cell (G. Urlaub and L. A., Chasin, Proc. Natl. Acad. Sci., U.S.A., 77, 4216–4220 (1980)), etc., while useful cells are not limited to these cells. Useful expression vectors of vertebrate cells are those having a promotor positioned upstream of the gene to be expressed, RNA splicing sites, polyadenylation site, transcription termination sequence, etc. These vectors may further have a replication origin when required. Examples of useful expression vectors include pSV2dhfr having an initial promotor of SV40 (S. Subramani, R. Mulligan and P. Berg, Mol. Cell. Biol., 1(9), 854–864 (1981)), which is not limitative.

Yeasts are widely used as eucaryotic microorganisms, among which those of the genus Saccharomyces are generally usable. Examples of popular expression vectors of yeasts and like eucaryotic microorganisms include pAM82 having a promotor for acid phosphatase gene (A. Miyanohara et al., Proc. Natl. Acad. Sci., U.S.A., 80, 1–5 (1983), etc.

$E.$ $coli$ and $Bacillus$ $subtilis$ are generally used as procaryotic hosts. The present invention employs, for example, plasmid vectors capable of replication in the host. To express the gene in the vector, expression plasmids can be used which have a promotor and SD (Shine-Dalgarno) base sequence at the upstream of the gene and ATG required for initiating protein synthesis. Widely used as host $E.$ $coli$ are $E.$ $coli$ K12 strain, etc. As a vector pBR322 is generally used. However, these are not limitative, and various known strains and vectors are usable. Examples of promoters usable are tryptophan promoter, $P_L$ promoter, lac promoter, lpp promotor, etc. The gene can be expressed with use of any of these promoters.

To describe the procedure with reference to the case wherein tryptophan promoter is used, vector pTM1 (Fumio Imamoto, Taisha, Vol. 22, 289 (1985)) having tryptophan promotor and SD sequence is used as an expression vector. A gene coding for a desired polypeptide and having ATG when required is linked to the site of restriction enzyme ClaI which is present downstream from the SD sequence. Incidentally, not only the direct expression system but a fusion protein expression system is also usable which employs, for example, $\beta$-galactosidase, $\beta$-lactamase or the like.

The expression vector thus obtained is introduced into host cells and thereby transformed by usual methods. For example, cells chiefly in the logarithmic growth phase are collected, treated with $CaCl_2$ and thereby made to readily accept DNA, whereupon the vector is introduced into the cell. With this method, $MgCl_2$ or RbCl can be made present conjointly with the vector so as to achieve an improved transformation efficiency, as is generally known. The cell can be converted to spheroplast or protoplast before transformation.

The desired transformant thus obtained can be incubated in the usual manner, whereby the desired polypeptide is produced and accumulated. The medium for the incubation may be any of those generally used for incubating cells, such as L medium, E medium, M9 medium, etc. Various carbon sources, nitrogen sources, inorganic salts, vitamins, etc. which are usually known can be admixed with these media. When the tryptophan promotor is used, M9 minimum medium, for example, is usable which has admixed therewith casamino acid for effecting the action of the promotor. A chemical, such as indoleacrylic acid, for enhancing the action of tryptophan promotor can be added to the medium at a suitable stage of incubation.

The desired polypeptide can be isolated from the resulting culture containing an active substance and purified by usual methods. It is desirable to extract the polypeptide from the host under a mild condition as by osmotic shock so as to maintain the higher-order structure thereof.

The above isolation or purification method is conducted substantially by various procedures utilizing the physical or chemical properties of the desired polypeptide. (See for example, "Biological Data Book II," pp. 1175–1259, 1st edition, 1st print, Jun. 23, 1980, published by Kabushiki Kaisha Tokyo Kagakudojin.) Examples of useful procedures are treatment with use of a usual protein precipitating agent, ultrafiltration, molecular sieve chromatography (gel filtration), liquid chromatography, centrifugation, electrophoresis, affinity chromatography, dialysis, and combinations of such procedures.

The above procedure can be done, for example, by the following method. The desired polypeptide is separated from the supernatant as partially purified. This partial purification is carried out, for example, by a treatment using as a protein precipitating agent an organic solvent such as acetone, methanol, ethanol, propanol or dimethylformamide (DMF), or an acid such as acetic acid, perchloric acid (PCA) or trichloroacetic acid (TCA), a treatment using a salting-out agent such as ammonium sulfate, sodium sulfate or sodium phosphate and/or ultrafiltration using a dialysis membrane, flat membrane, hollow fiber membrane or the like. These treatments are conducted in the same manner as usually done under usual conditions.

The roughly purified product thus obtained is then subjected to gel filtration, whereby a fraction exhibiting the activity of the desired substance is collected. Useful gel filtration agents are not limited specifically. Such agents include those made of dextran gel, polyacrylamide gel, agarose gel, polyacrylamideagarose gel, cellulose or the like. Examples of useful agents commercially available are Sephadex G type, Sephadex LH type, Sepharose type, Sephacryl type (all products of Pharmacia), Cellofine (Chisso Corporation), Biogel P type, Biogel A type (both product of Bio-Rad Lab), Ultro gel (LKB), TSK-G type (product of Tosoh Corporation), etc.

The above-specified polypeptide, i.e., IL-1α derivative can be isolated from the fraction as a homogeneous substance, for example, by subjecting the active fraction obtained by gel filtration to affinity chromatography with use of a hydroxyapatite column, ion exchange column chromatography as of the DEAE, CM or SP method, chromatofocusing method, reverse-phase high-performance liquid chromatography or the like, or to a combination of such methods.

The present medicament for treating thrombocytopenia requires the presence of IL-1α, IL-1β or their derivative as an active component and may further contain pharmaceutical ingredients which are used in usual medicaments. Pharmaceutical compositions can be prepared in a usual manner by mixing the active component with, other components and conventional pharmaceutical excipients as desired, and can be in any of various dosage forms in accordance with the contemplated purpose of treatment.

Particularly in view of stabilization of the IL-1 active substance, preferable as other components to be used in combination with said active substance are, for example, albumins such as human serum albumin (HSA), usual L form amino acids such as cysteine and glycine, etc. The amount of such component to be used is not specifically limited, but is usually about 0.01 to about 10 mg per microgram of the IL-1 active substance in case of albumin, and about 0.001 to about 10 mg per 1 µg of the active substance in the case of amino acid (calculated as the total amount of amino acids in the case of use where not less than 2 amino acids are used). If required, the pharmaceutical composition may comprise, for example, sugars including monosaccharides such as glucose, mannose, galactose and fluctose, sugar alcohols such as mannitol, inositol and xylitol, disaccharides such as sucrose, maltose and lactose, polysaccharides such as dextran and hydroxypropyl starch (of the above sugars, sucrose, maltose, mannitol, inositol, dextran, etc. are preferable); ionic or nonionic surfactants such as surfactants of polyoxyethylene glycol sorbitan alkyl ester type, polyoxyethylene alkyl ether type, sorbitan monoacyl ester type and fatty acid glyceride type. The sugars as such are usually blended in an amount of not less than about 0.1 mg, preferably about 1 to about 100 mg, per µg of the IL-1 active substance. The surfactant is usually blended in an amount of not less than about 0.0001 mg, preferably about 0.001 to about 0.1 mg, per µg of the IL-1 active substance.

Medicinal preparations are formulated usually in the form of pharmaceutical compositions comprising a pharmacologically effective amount of the IL-1 derivative (i.e., IL-1α, IL-1β and their derivatives) and, if required, a suitable carrier. Examples of useful pharmaceutical carriers include diluents and excipients such as filler, extender, binder, wetting agent, disintegrator which are generally used for preparing pharmaceuticals of the desired form to be used. The form of the pharmaceutical compositions is not specifically limited insofar as they effectively contain the present IL-1 active substance as the active component but can be, for example, in the form of tablets, powder, granules, pills or like solid preparation. Usually, however, it is suitable that the composition be in the form of a solution, suspension, emulsion or the like for injection. Alternatively, such a composition can be a dry product which can be made liquid with addition of a suitable carrier before use. The pharmaceutical compositions mentioned above can be prepared by usual methods.

Buffers are also used as carriers. The buffers are not limited specifically and preferably include citric acid-sodium phoshate, citric acid-sodium citrate, acetic acid-sodium acetate, sodium hydrogenphosphate-sodium dihydrogenphosphate, citric acid-borax, and like buffer with pH 4–8, preferable pH 5–6.

In accordance with the form of the pharmaceutical composition obtained, the composition is administered via a suitable route. For example, those for injection are given intravenously, intramuscularly, subcutaneously, intracuteneously, intraperitoneally or otherwise. The solid composition is given orally or intrasectally. The amount of the active component of the composition and the dosage of the composition are suitably determined according to the method and form of administration, purpose of use, symptoms of the patient, etc. and are not definitely determinable. It is generally desirable to incorporate about 0.00001 to about 80 wt. % of the active component into the pharmaceutical preparation and to give the preparation at a daily dose of about 0.01 µg to about 10 mg, calculated as the active component, for adults. The preparation need not always be given only once a day but can be given in three to four divided doses daily.

The present invention will be described in greater detail with reference to the following preparation examples and examples.

In these examples, the physiological activity was determined by the following method.

(1) Determination of IL-1 activity

Expressed in terms of LAF activity as measured by the method of J. J. Oppenhein et al. (J. Immunol., 116, 1466 (1976)) using thymus cells of a mouse of C3H/HeJ strain.

(2) Determination of GIF activity

Portions (0.1 ml) of the test solution diluted to varying concentrations were placed into the wells of 96-well microplate (Corning Co., Ltd.), 0.1 ml of Eagle's MEM suspension containing 10% FCS comprising human melonoma cells A375 in an amount of $2\times10^4$ cells/ml was then placed into each well, and the cells were incubated in a $CO_2$ incubator (Napco Co., Ltd.) for 4 days. After the incubation, 0.05 ml of 0.05% Neutral Red (Wako Junyaku Co., Ltd.) was placed into each well, followed by incubation at 37° C. for 2 hours. After removing the supernatant, 0.3 ml of phosphate buffer saline was gently poured into each well for washing. After removing the washing, 0.1 ml of mixture of sodium dihydrophosphate and ethanol in equal amounts was placed into each well, the plate was shaken for several minutes by a micromixer, and the amount of pigment taken into the cell was measured at 540 mµ using a photometer for 96-well microtitration plates (Titer check multiscan, Flow Lab.) to determine growth inhibition activity. As the GIF activity unit was taken the reciprocal of the number of times of dilution, when the test group exhibited 50% of the inhibition of cell growth of the control group, i.e., the test group exhibited ½ the absorbance measured of the control group. Accordingly, for example, when the GIF activity is 10 units, the test solution, even if diluted ten-fold, still has activity to inhibit cell growth 50%.

The following drawings are referred to in the examples.

FIGS. 1 and 2 show the results of obtained by testing the effect to inhibit pyretogenesis in various IL-1's.

PREPARATION EXAMPLE 1

Preparation of IL-1α Derivative (16G.36D.141S)

(1) Preparation of Plasmid for Expressing IL-1α Derivative

Plasmid ptrp IL-1α-141S used in this example was prepared in the same manner as described in European Patent Publication No. 237073, by the site-specific mutagenesis method (Proc. Natl. Acad. Sci.,81, 5662–5666 (1984)), using plasmid ptrp IL-1α-113 obtained from pTM1 (Fumio ImanToto, Taisha, 22, 289, (1985)) and plasmid pcD-GIF-207 (carried by *E. coli*χ1776/pcD-GIF-207 (FERM BP-1294)) having cDNA coding for an IL-1α precursor protein. Plasmid ptrp IL-1α-141S carries a gene coding for a IL-1α derivative having the amino acid sequence of the formula (A) in which Cys at the 141-position was replaced by Ser.

ClaI/BamHI DNA fragment (527 bp) was isolated from plasmid ptrp IL-1α-141S and ligated with ClaI/BamHI large fragment of IL-1β site specific-mutagenesis vector fl.IL-1β lppt (Biochem. Biophys. Res. Commun., 150, 1106–1114 (1988)) to obtain fl.IL-1α-141S. Helper phage M13KO7 (Takara Shuzo Co. Ltd.) was infected with the above product to obtain single-strand (ss,) DNA, which was then used as a mutagenesis template.

Using as a primer a synthetic oligonucleotide [5'-ACTTTATGGGGATCATCA-3'] 5'-phosphorylated with T4 polynucleotide kinase, site-specific mutagenesis was carried out by oligonucleotide-directed in vitro mutagenesis (Amersham UK, code RPN. 2322).

A ss DNA was obtained from the clone transformed into *E. coli* MV1304 (Takara Shuzo Co. Ltd.) and subjected to DNA sequencing by deoxy chain termination to obtain recombinant (transformant) fl.IL-1α-16G.141S/*E. coli* MV1304.

This plasmid is the expression plasmid of polypeptide of the formula (α) in which Arg at the 16-position was replaced by Gly, X at the 36-position was Asn, and Y at the 141-position was Ser.

The transformant has been deposited under the name of Escherichia coli MV1304/fl.IL-1α.16G.141S and deposition number FERM BP-2434 in Fermentation Research Institute, Agency of Industrial Science and Technology.

(2) Incubation of transformant

The transformant obtained in (1), i.e., *E. coli* MV1304/fl.IL-1α-16G.141S was incubated overnight at 37° C. with shaking in 600 ml of LB medium (of the following composition) containing 100 μg/ml of ampicillin, giving pre-culture solution.

<Composition of LB medium>

| | |
|---|---|
| Bacto tryptone (product of Difco) | 10 g/l |
| Bacto yeast extract (ibid.) | 5 g/l |
| NaCl (Wako Pure Chemical Inc. Ltd.) | 10 g/l |

A 600 ml portion of the pre-culture solution was inoculated into 30 l of a production medium of the following composition and incubated at 36.5° C. for 14 hours in a 50-l jar fermenter (product of Hitachi Ltd.) with shaken aeration of 0.5 VVM at 120 rpm.

<Composition of production medium>

| | |
|---|---|
| $Na_2HPO_4 \cdot 12H_2O$ | 6 g/l |
| $KH_2PO_4$ | 3 g/l |
| NaCl | 0.5 g/l |
| $NH_4Cl$ | 1 g/l |
| Bacto casamino acid | 10 g/l |
| Bacto yeast extract | 0.5 g/l |
| L-cysteine.HCl | 75 mg/l |
| L-proline | 75 mg/l |
| L-leucine | 75 mg/l |

(The medium was adjusted to pH 7.4 with 4N NaOH followed by treatment in an autoclave at 121° C. for 30 minutes or by treatment with steam-heating at 123° C. for 20 minutes. The sterilized solution of the following composition was added aseptically to the medium when inoculated.

<Composition of sterilized solution>

| | |
|---|---|
| 1M $MgSO_4 \cdot 4H_2O$ | 2 ml/l |
| 1M $CaCl_2 \cdot 2H_2O$ | 0.1 ml/l |
| 7.5 mg/l Thiamine.HCl | 1 ml/l |
| 40% Glucose | 18.75 ml/l) |

After incubation, the suspension of *E. coli* in 300 ml of 1M $Na_2HPO_4$ was allowed to stand overnight in a refrigerator and dialyzed against 10 mM tris HCl buffer (pH 8.0) for 2 days in the same refrigerator. The dialyzate was centrifuged at 16000×g to separate a supernatant from a precipitate.

(3) Purification of IL-1α derivative

The cell extract supernatant prepared as above (2) was adjusted to pH 3 with 2M acetic acid and purified using SP-HPLC (TSK Gel SP-5PW column, 5.5 cm in diameter and 20 cm in length, product of Tosoh Corporation) under the following conditions.

Column: TSK Gel SP-5PW (5.5×20 cm, Tosoh Corporation)
Eluent A: 50 mM Sodium acetate (pH 4.5)
Eluent B: 50 mM Sodium acetate (pH 5.5)
Flow rate: 30 ml/min.

| Concentration gradient: | Time (min) | % B |
|---|---|---|
| | 0 | 0 |
| | 30 | 0 |
| | 130 | 100 |
| | 160 | 100 |
| | 165 | 0 |
| | 195 | 0 |

The above procedure resulted in a GIF active fraction with a retention time of 114 to 131 minutes.

The active fraction obtained was subjected to SP-HPLC again under the same conditions as described above to give a GIF active fraction.

The active fraction collected was purified by ion-exchange chromatography (DEAE-HPLC) under the following conditions:

Column: TSK Gel DEAE-5PW (5.5×20 cm, Tosoh Corporation)
Eluent A: 20 mM Tris HCl buffer (pH 8.0)
Eluent B: 20 mM Tris HCl buffer (pH 8.0)+0.5M NaCl
Flow rate: 30 ml/min.

| Concentration gradient: | Time (min) | % B |
|---|---|---|
| | 0 | 0 |
| | 30 | 0 |
| | 150 | 60 |
| | 155 | 100 |

-continued

| Concentration gradient: | Time (min) | % B |
|---|---|---|
| | 185 | 100 |
| | 190 | 0 |

The above procedure resulted in a GIF active fraction with a retention time of 98.8 to 102.8 minutes.

The active fraction collected was then subjected to ultrafiltration (YM-5 Membrane, product of Amikon) to prepare a concentrated product with an isoelectric point (PI) of 5.0. During the above ultrafiltration, portions of the buffer were exchanged so that the buffer finally had the same composition as 20 mM sodium phosphate buffer (pH 7.0).

(4) Identification of IL-1α Derivative
Amino acid composition

The concentrated product (30 μl) obtained in (3) was carefully placed into the bottom of a thick-walled hard test tube, 6 mm×50 mm, and the test tube was placed in a reaction vial and dried in a vacuum with Pico Tag Work Station (product of Warters). A 200 μl quantity of 6N HCl (containing 1% phenol) was replaced into the test tube within the vial. The interior of the vial was carefully deaerated and then sealed off to effect hydrolysis at 130° C. over a period of 4 hours.

After opening the tube, 400 μl of 0.02N hydrochloric acid was added to the hydrolyzate, and the resulting mixture was employed as a specimen solution for amino acid analysis.

A 250 μl quantity of the specimen solution was used for amino acid analysis by an amino acid analyzer (Model HITACHI 835, product of Hitachi Ltd.). The amino acids separated were detected by the o-phthalaldehyde method and quantitatively determined with reference to calibration curves prepared with use of authentic amino acids.

Table 1 shows the results in terms of the mole ratio of component amino acids based on Phe (10 moles). Under the above analysis conditions, Pro, Cys and Trp are not determinable.

TABLE 1

| Amino acid | Mole ratio |
|---|---|
| Asp and/or Asn | 21.1 |
| Thr | 11.2 |
| Ser | 11.5 |
| Glu and/or Gln | 18.3 |
| Gly | 8.8 |
| Ala | 14.3 |
| Val | 6.8 |
| Met | 2.0 |
| Ile | 10.4 |
| Leu | 15.2 |
| Tyr | 6.7 |
| Phe | (10) |
| Lys | 11.1 |
| His | 3.2 |
| Arg | 2.7 |

Amino acid sequence

A 50 μl (298 pmol) quantity of the concentrated product obtained in (3) was analyzed by a protein sequencer, Model 470A (Applied Biosystems Inc.). Each resulting PTH-amino acid was suitably diluted with 100 to 500 μl of 33% aqueous acetonitrile solution, and 5-pl portion of the dilution was injected into a chromatographic column by an autosampler, Waters 710B. For the chromatographic system, two pumps, Beckman Model 112, were operated by a controller, Model 421. The column used, measuring 2 mm×250 mm and packed with Ultrasphere ODS-5 μm, was maintained at 55° C. by a column heater. The flow rate was 0.3 ml/min. A mixture of 20 mM sodium acetate and acetonitrile was used for gradient elution. Absorbance was monitored at 269 nm. Analysis was conducted for 45 minutes.

The results of analysis revealed that the concentrated product obtained by the procedure (3) had the following sequence of 36 amino acids at the N terminal.

Ser—Ala—Pro—Phe—Ser—Phe—Leu—Ser—Asn—Val—
Lys—Tyr—Asn—Phe—Met—Gly—Ile—Ile—Lys—Tyr—
Glu—Phe—Ile—Leu—Asn—Asp—Ala—Leu—Asn—Gln—
Ser—Ile—Ile—Arg—Ala—Asp

The above result confirms that the purified product obtained is a polypeptide of the formula (α) (IL-1α) which is as modified in that Arg at the 16-position was replaced by Gly.

Although the 36-position amino acid was Asn in the gene, it was Asp in the purified product. This finding suggests that the derivative wherein the 36-position amino acid is Asp is a stable one as observed in native IL-1α, and that the same mutagenesis occurs in this IL-1α derivative as in native IL-1α.

PREPARATION EXAMPLE 2

Preparation of IL-1α Derivative (Δ(1–14) .36D.141S)

(1) Preparation of Plasmid for Expressing IL-1α Derivative

Using plasmid ptrp IL-1α.36D.141S (European Patent Publication No. 237073, carried by *Escherichia coli* HB101/ IL-1α-36D.141S (FERM BP-1295)), the procedure was done by site-specific mutagenesis method.

ClaI/BamHI DNA fragment (527 bp) was isolated from plasmid ptrp IL-1α-36D.141S and ligated with the same ClaI/BamHI large fragment of vector fl.IL-1β lppT as in Preparation Example 1 to obtain fl.IL-1α-36D.141S. With the product obtained was infected helper phage M13KO7 (Takara Shuzo Co. Ltd.) to obtain single-strand (ss) DNA, which was then used as a mutagenesis template.

Using as a primer a synthetic oligonucleotide [5'-AAGGGTATCGATTATGATGAGGATCATC-3'], site-specific mutagenesis was carried out by oligonucleotide-directed in vitro mutagenesis in the same manner as in Preparation Example 1.

A ss DNA obtained from the clone transformed into *E. coli* MV1184 (Takara Shuzo Co., Ltd.) was subjected to DNA sequencing by dideoxy chain termination to obtain recombinant (transformant) fl.IL-1α-Δ(1–14).36D.141S/*E. coli* MV1184.

This plasmid is the expression plasmid of polypeptide of the formula (α) which is modified in that the sequence of the 1- to 14-position amino acids is deleted, the 36-position X is Asp and the 141-position Y is Ser.

The transformant has been deposited under the name of *Escherichia coli* MV1184/fl.IL-1α.Δ(1–14)36D.141S and deposition number FERM BP-2433 in Fermentation Research Institute, Agency of Industrial Science and Technology.

Expression and purification of the desired IL-1α derivative were performed substantially in the same manner as in Preparation Example 1.

The desired derivative (IL-1α-Δ(1–14).36D.141S) was thus obtained.

The specific activity was $1.0 \times 10^6$ GIF units/mg of protein.
(2) Identification of IL-1α Derivative
Amino acid composition The IL-1α derivative obtained in (1) was subjected to amino acid analysis in the same manner as in Preparation Example 1.

Table 2 shows the results in terms of the mole ratio of component amino acids based on Phe (9 moles).

TABLE 1

| Amino acid | Mole ratio |
| --- | --- |
| Asp | 19.0 |
| Thr | 11.0 |
| Ser | 7.1 |
| Glu | 16.3 |
| Gly | 5.3 |
| Ala | 13.2 |
| Val | 5.8 |
| Met | 4.0 |
| Ile | 10.3 |
| Leu | 13.8 |
| Tyr | 5.7 |
| Phe | (7) |
| Lys | 10.0 |
| His | 3.2 |

Amino acid sequence

The amino acid sequence at the N-terminal of the IL-1α derivative obtained in (1) was analyzed in the same manner as in Preparation Example 1.

The result revealed the following sequence of 15 amino acids at the N terminal.

Met-Met-Arg-Ile-Ile-Lys-Tyr-Glu-Phe-Ile-Leu-Asn-Asp-Ala-Leu

The above result confirms that the derivative obtained has a sequence of IL-1α of the formula (α) which is modified in that the sequence of the 1- to 14-position amino acids is deleted.

PREPARATION EXAMPLE 3

Preparation of IL-1α Derivative (Δ(1–15))

(1) Preparation of Plasmid for Expressing IL-1α Derivative

Vector fl.IL-1β lppT for IL-1β site specific-mutagenesis (Biochem. Biophys. Res. Commun., 150, 1106–1114 (1988)) was used in this example. First this vector was digested with EcoRI, treated with DNA polymerase I (Klenow fragment) and subjected to self-ligation, giving fl.IL-1β lppTARI in which EcoRI site was deleted. From this plasmid HpaI/BamHI large fragment was excised.

EcoRI/BamHI DNA small fragment was excised from plasmid ptrp IL-1α-113 (European Patent Publication No. 237073) and ligated with the above HpaI/BamHI large fragment using a synthetic linker (5'-AACTAGTACGCAAGTT CACGTAAGGAGGTTTAATATTATGAGAATCATCAAA-TACG-3' and 5'-AATTCGTATTTGATGATT- CTCAT- AATATTAAACCTCCTTACGTGAACTTGCGTACTAG TT-3') to give the desired recombinant (transformant) fl.IL-1α.Δ(1–15)/E. coli MV1184.

This plasmid is an expression plasmid of the present IL-1α derivative having an amino acid sequence of the formula (α) wherein the sequence of the 1- to 15-position amino acids was deleted, the 36-position X is Asn, and the 141-position Y is Cys.

(2) Preparation of IL-1α Derivative

Using the plasmid obtained above, expression and purification of the desired IL-1α derivative were carried out substantially in the same manner as in Preparation Example 1.

E. coli HB101 having plasmid fl.IL-1α.Δ(1–15) was cultured under the same conditions as in Preparation Example 1. The cells were harvested by centrifugation at 16000×g and suspended in 1M phosphate buffer (pH 6.0). The suspension was allowed to stand overnight in a cold room and dialyzed against 0.01M phosphate buffer (pH 6.0) for two days. The dialyzate was centrifuged at 16000×g to separate a supernatnat and a precipitate.

The resulting precipitate was subjected twice to the same operation as described above. The two supernatants obtained were mixed together, and the mixture was subjected to purification as follows.

(3) Purification of IL-1α Derivative

The supernatant prepared as above (2) was purified using DEAE-HPLC (TSK Gel DEAE-5PW column, 5.5 cm in diameter and 20 cm in length, product of Tosoh Corporation) under the following conditions.

Column: TSK Gel DEAE-5PW (5.5×20 cm, Tosoh Corporation)
Eluent A: 20 mM Tris HCl (pH 8.0)
Eluent B: 20 mM Tris HCl (pH 8.0) containing 0.5M NaCl
Flow rate: 30 ml/min.

| Concentration gradient: | Time (min) | % B |
| --- | --- | --- |
| | 0 | 0 |
| | 30 | 0 |
| | 150 | 60 |
| | 155 | 100 |
| | 185 | 100 |

The fraction with a retention time of 88 to 93 minutes (fraction A) and the fraction with a retention time of 99 to 103 (fraction B) were collected and then subjected to ultrafiltration (YM-5 Membrane, product of Amikon) to concentrate. The concentrate was purified by gel filtration-HPLC (TSK Gel G-2000 SWG column, 21.5×600 mm, Tosoh Corporation, eluent: PBS⁻).

Fraction A purified above was adjusted to pH 4.0 with 2M acetic acid and subjected to SP-HPLC (TSK GEl SP-5PW column, 21.5×150 mm, Tosoh Corporation) under the following conditions.

Column: TSK Gel SP-5PW (21.5×150 cm, Tosoh Corporation)
Eluent A: 50 mM sodium acetate (pH 5.0)
Eluent B: 50 mM sodium acetate (pH 5.0) containing 0.5M NaCl
Flow rate: 3 ml/min.

| Concentration gradient: | Time (min) | % B |
| --- | --- | --- |
| | 0 | 0 |
| | 20 | 0 |
| | 110 | 45 |
| | 115 | 100 |
| | 130 | 100 |
| | 135 | 0 |

The fraction with a retention time of 87 to 93 minutes was collected and then concentrated by ultrafiltration (YM-5 Membrane, product of Amikon). During the ultrafiltration, the buffer was exchanged in limited amounts so as to have finally the same composition as that of 20 mM sodium phosphate concentrate (pH 6.0).

(4) Identification of IL-1α Derivative (Fraction A)

Amino acid composition.

The purified concentrate obtained in (3) was subjected to amino acid analysis in the same manner as in Preparation Example 1.

Table 3 shows the results in terms of the mole ratio of component amino acids based on Phe (7 moles).

TABLE 3

| Amino acid | Mole ratio |
| --- | --- |
| Asp | 18.0 |
| Thr | 11.2 |
| Ser | 6.8 |
| Glu | 17.1 |
| Gly | 5.8 |
| Ala | 13.1 |
| Val | 5.7 |
| Met | 2.8 |
| Ile | 10.9 |
| Leu | 14.1 |
| Tyr | 5.9 |
| Phe | (7) |
| Lys | 10.2 |
| His | 3.0 |
| Arg | 3.1 |

Amino acid sequence

The amino acid sequence at the N terminal of the IL-1α derivative prepared in (3) was analyzed in the same manner as in Preparation Example 1.

The results of analysis revealed the following sequence of 23 amino acids at the N-terminal.

Met-Arg-Ile-Ile-Lys-Tyr-Glu-Phe-Ile-Leu-Asn-Asp-Ala-Leu-Asn-Gln-Ser-Ile-Ile-Arg-Ala-Asn-Asp

The above result confirms that the derivative obtained has a sequence of the formula (α) (IL-1α) wherein the sequence of the 1- to 15-position amino acids is deleted, and X is Asn.
(Fraction B)
Amino Acid Composition The purified product was prepared and subjected to amino acid analysis in the same manner as described in fraction A.

Table 4 shows the results in terms of the mole ratio of component amino acids based on Phe (7 moles).

TABLE 3

| Amino acid | Mole ratio |
| --- | --- |
| Asp | 18.3 |
| Thr | 11.3 |
| Ser | 6.7 |
| Glu | 17.2 |
| Gly | 5.7 |
| Ala | 13.2 |
| Val | 5.8 |
| Met | 2.9 |
| Ile | 10.9 |
| Leu | 14.1 |
| Tyr | 5.9 |
| Phe | (7) |
| Lys | 9.9 |
| His | 3.0 |
| Arg | 3.1 |

Amino acid sequence

The amino acid sequence at the N terminal of the purified product of fraction B was analysed in the same manner as in Preparation Example 1. The sequence of 23 amino acids at N-terminal as follows.

Met — Arg — Ile — Ile — Lys — Tyr — Glu — Phe — Ile — Leu —
Asn — Asp — Ala — Leu — Asn — Gln — Ser — Ile — Ile — Arg —
Ala — Asp — Asp —

The result confirms that the derivative obtained has the sequence of the formula (α) wherein the sequence of the 1- to 15- position amino acids is deleted and X is Asp.

PREPARATION EXAMPLE 4

Preparation of IL-1α Derivative (Δ(1–15).36D.141S)

(1) Preparation of Expression Vector pAT-IL-1αΔ(1–15)36D.141S

Using plasmid ptrp IL-1α-36D.141S (European Patent Publication No. 237073, carried by Escherichia coli HB101/IL-1α-36D.141S (FERM BP-1295)), the procedure was done by the site-specific mutagenesis method.

ClaI/BamHI DNA fragment (527 bp) was excised from plasmid ptrp IL-1α-36D.141S and ligated with ClaI/BamHI large fragment of IL-1β site specific-mutagenesis vector fl.IL-1β lppT (Biochem. Biophys. Res. Cpmmun., 150 1106–1114 (1988)), giving fl.IL-1α-36D.141S. Helper phage M13KO7 (Takara Shuzo Co., Ltd.) was infected with the above plasmid to obtain single-strand (ss) DNA, which was then used as a mutagenesis template.

Using as a primer a synthetic oligonucleotide [5'-GTATCGATAATGAGAATCATC-3'], site-specific mutagenesis was carried out by Oligonucleotide-directed in vitro Mutagenesis KIT (product of Amersham UK).

A ss DNA was obtained from the clone transformed into E. coli MV1184 (Takara Shuzo Co., Ltd.) was subjected to DNA sequencing by dideoxy chain termination to obtain recombinant (transformant) fl.IL-1αΔ(1–15).36D.141S/E. coli MV1184.

Expression vector for large volume fermentation was prepared as follows.

At first, fl.IL-1β lppT was digested with MluI and SalI, treated with DNA polymerase (Klenow fragment) and ligated with T4 DNA ligase, giving fl.IL-1β lppTΔMS. This product was treated with EcoRI and then DNA polymerase (Klenow fragment), subjected to self ligation and further treated with AatII, T4DNA polymerase and BglII linker (pGAAGATCTTC) in that order to convert AatII site into BglII site. The plasmid was further treated with SalI, DNA polymerase (Klenow fragment) and XbaI linker (pGCTCTAGAGC) to convert SalI site to XbaI site. ClaI/BamHI DNA large fragment (5.5 Kb) was excised from the resulting plasmid and ligated with ClaI/BamHI DNA fragment (482 bp) of fl.IL-1αΔ(1–15)36D.141S, giving fl.IL-αΔ(1–15)36D.141S (AatII→BglII, SalI→XbaI) from which BglII/XbaI DNA fragment (1109 bp) was excised.

Furthermore, plasmid pAT153 was treated to convert ClaI site into BglII site and DraI site into XbaI site and digested with BglII and XbaI to give BglII/XbaI large fragment (2514 bp). The large fragment was ligated with the above BglII/XbaI fragment (1109 bp), affording the desired transformant pAT.IL-1αΔ(1–15)36D 141S.

This transformant is the expression plasmid having the amino acid sequence of the formula (α) in which the sequence of the 1- to 15- position amino acids is deleted (However, the protein obtained from this transformant, since Met derived from the initiation codon is attached to the N terminal of the protein, can be the polypeptidein which the sequence of the 1- to 14-position amino acids is deleted), the 36-position X is Asp and the 141-position Y is Ser.

The transformant has been deposited under the name of Escherichia coli HB101/pAT IL-1αΔ(1–15)36D 141S and deposition number FERM BP-2483 in Fermentation Research Institute, Agency of Industrial Science and Technology.

(2) Incubation of transformant

The transformant obtained in (1), i.e., E. coli HB101/pAT.IL-αΔ(1–15)36D.141S was incubated overnight at 37° C. with shaking in 600 ml of LB medium of the following composition containing 10 μg/ml of tetracycline, giving pre-culture solution.

<Composition of LB medium>

| | |
|---|---|
| Bacto tryptone (product of Difco) | 10 g/l |
| Bacto yeast extract (ibid.) | 5 g/l |
| NaCl (Wako Pure Chemical Inc. Ltd.) | 10 g/l |

A 600 ml portion of the pre-culture solution was inoculated in 30 l of a production medium of the following composition and incubated at 36.5° C. for 16 hours in a 50-l jar fermenter (product of Hitachi Ltd.) with shaken aeration of 1.0 VVM at 300 rpm.

<Composition of production medium>

| | |
|---|---|
| $Na_2HPO_4 \cdot 12H_2O$ | 6 g/l |
| $KH_2PO_4$ | 3 g/l |
| NaCl | 0.5 g/l |
| $NH_4Cl$ | 1 g/l |
| Acid hydrolyzate of caseine (product of Sigma) | 10 g/l |
| Bacto yeast extract | 0.5 g/l |
| $MnCl_2 \cdot 4H_2O$ | 2.5 mg/l |
| L-cysteine.HCl | 75 mg/l |
| L-proline | 75 mg/l |
| L-leucine | 75 mg/l |

(The medium was adjusted to pH 7.4 with 4 N NaOH, followed by treatment in an autoclave at 121° C. for 30 minutes. The sterilized solution of the following composition was added aseptically to the medium when inoculated.

<Composition of sterilized solution>

| | |
|---|---|
| 1M $MgSO_4 \cdot 4H_2O$ | 2 ml/l |
| 1M $CaCl_2 \cdot 2H_2O$ | 0.1 ml/l |
| 7.5 mg/l Thiamine.HCl | 1 ml/l |
| 40% Glucose | 18.75 ml/l) |

After incubation, cells were harvested by centrifugation at 16000×g. The suspension of the cells in 1M phosphate buffer (pH 6.0) was allowed to stand overnight in a refrigerator and dialyzed against 10 mM tris HCl buffer (pH 8.0) for 2 days. The dialyzate was centrifuged at 16000×g to separate a supernatant from a precipitate. The precipitate was treated by the same operation as above to give a supernatant. The supernatants thus obtained were mixed together, and the mixture was subjected to purification procedure as follows.

(3) Purification of IL-1α derivative

The cell extract supernatant prepared as above (2) was adjusted to pH 3 with 2M acetic acid and purified using SP-HPLC (TSK Gel SP-5PW column, 5.5 cm in diameter and 20 cm in length, product of Tosoh Corporation) under the following conditions.
Column: TSK Gel SP-5PW (5.5×20 cm, Tosoh Corporation)
Eluent A: 50 mM Sodium acetate (pH 5.0)
Eluent B: 50 mM Sodium acetate (pH 5.0)+0.5M NaCl
Flow rate: 30ml/min.

| Concentration gradient: | Time (min) | % B |
|---|---|---|
| | 0 | 0 |
| | 30 | 0 |
| | 90 | 30 |
| | 95 | 100 |
| | 125 | 100 |
| | 130 | 0 |

The active fractions with retention time of 70 to 75 minutes were collected and adjusted to pH 8.1 with 1M Tris HCl buffer. The fraction was applied to a DEAE-HPLC column (TSK GEL DEAE-5PW column, 5.5×20 cm, product of Tosoh Corporation), followed by elution under the following conditions.
Column: TSK Gel DEAE-5PW (5.5×20 cm, Tosoh Corporation)
Eluent A: 20 mM Tris HCl (pH 8.0)
Eluent B: 20 mM Tris HCl (pH 8.0)+0.5M NaCl
Flow rate: 30 ml/min.

| Concentration gradient: | Time (min) | % B |
|---|---|---|
| | 0 | 0 |
| | 20 | 0 |
| | 140 | 60 |
| | 145 | 100 |
| | 165 | 100 |
| | 170 | 0 |

The active fractions with retention time of 92 to 96 minutes were collected, concentrated by ultrafiltration (YM-5 membrane) and purified by gel filtration-HPLC (TSK-Gel G-2000SWG column, 21.5×600 mm, product of Tosoh Corporation, eluent: $PBS^-$).

The purified product was adjusted to pH 4 with 2M acetic acid and applied to a SP-HPLC column (TSK GEL SP-5PW column, 21.5×150 mm, product of Tosoh Corporation), followed by elution under the following conditions.
Column: TSK Gel SP-5PW (21.5×150 mm, Tosoh Corporation)
Eluent A: 50 mM Sodium acetate (pH 5.0)
Eluent B: 50 mM Sodium acetate (pH 5.0)+0.5M NaCl
Flow rate: 3 ml/min.

| Concentration gradient: | Time (min) | % B |
|---|---|---|
| | 0 | 0 |
| | 20 | 0 |
| | 110 | 45 |
| | 115 | 100 |
| | 130 | 100 |
| | 135 | 0 |

The active fractions with retention time of 87 to 90 minutes were collected and then subjected to ultrafiltration (YM-5 Membrane, product of Amikon) to prepare a concentrated product. During the above ultrafiltration, small portions of the buffer were exchanged so that the buffer finally had the same composition as 20 mM sodium phosphate buffer (pH 7.0).

(4) Identification of IL-1α Derivative
Amino acid composition

The purified product obtained in (3) was subjected to amino acid analysis in the same manner as in Preparation Example 1.

Table 5 shows the result in terms of the mole ratio of component amino acids based on Phe (7 moles).

TABLE 5

| Amino acid | Mole ratio |
|---|---|
| Asp | 18.6 |
| Thr | 11.4 |
| Ser | 7.7 |
| Glu | 17.2 |
| Gly | 5.7 |
| Ala | 13.2 |
| Val | 5.8 |

TABLE 5-continued

| Amino acid | Mole ratio |
| --- | --- |
| Met | 2.8 |
| Ile | 10.9 |
| Leu | 14.1 |
| Tyr | 5.9 |
| Phe | (7) |
| Lys | 9.9 |
| His | 3.0 |
| Arg | 3.1 |

Amino acid sequence

The amino acid sequence at the N-terminal of the IL-1α derivative prepared in (3) was analyzed.

The results of analysis revealed the following sequence of 15 amino acids at the N terminal.

Met-Arg-Ile-Ile-Lys-Tyr-Glu-Phe-Ile-Leu-Asn-Asp-Ala-Leu-Asn-

The above result confirms that the derivative has a sequence of the formula (α) (IL-1α) in which the sequence of the 1- to 15-position amino acids was deleted.

PREPARATION EXAMPLE 5

Preparation of IL-1α Derivative (24-153)

(1) Preparation of Expression Plasmid

Using plasmid ptrp GIF-α which carries a gene coding for human IL-1α (this plasmid is disclosed in European Patent Publication EP0187991, and E. coli transformed by this plasmid has been deposited under the name of Escherichia coliχ1776/ptrp GIF-α and deposition number FERM BP-949 in Fermentation Research Institute, Agency of Industrial Science and Technology since Dec. 12, 1985.), the desired expression plasmid of the desired polypeptide was constructed.

More specifically, ptrp GIF-α was digested with restriction enzymes NdeI and SalI, and then 781 bp of the DNA fragment which carries the region coding for the sequence of from the 24-position to the N-terminal amino acids of the IL-1β was isolated by agarose gel electrophoresis. The DNA fragment was treated with DNA polymerase I (Klenow fragment) to convert the restriction sites by the restriction enzymes NdeI and SalI into blunt ends.

The linkers (5'-CGATAATG-3' and 5'-CATTAT-3') 5'-phosphorylated with T4 polynucleotide kinase were ligated with the blunt ends of the above DNA fragment using T4 DNA ligase, followed by digestion with restriction enzymes ClaI and BamHI. The resulting plasmid was subjected to agarose gel electrophoresis, the DNA fragment (510 bp) was isolated.

Plasmid pTM1 was cut with restriction enzymes ClaI and BamHI and then subjected to agarose gel electrophoresis to isolate the DNA fragment (about 4.4 kbp) carrying trp promoter. This DNA fragment was ligated with the above 510 bp of ClaI/BamHI DNA fragment using T4 DNA ligase, followed by transforming into E. coli HB101. The desired transformant was selected by restriction enzyme analysis of plasmid DNA obtained by the boiling method (T. Maniatis, E. F. Fritsch and J. Sambrook, Molecular Cloning, pp366, Cold Spring Harbor Laboratory (1982)).

(2) Incubation of Transformant

The above transformant (E. coli HB101/ptrp GIF-α-24-153) was incubated overnight at 37° C. with shaking in 10 ml of LB medium (1% tryptone, 0.5% yeast extract and 0.5% NaCl) containing 50 µg/ml of ampicillin and 20 µg/ml of L-tryptophan. One ml portion of the culture was inoculated into 50 ml of M9 minimum medium (0.6% $Na_2HPO_4$, 0.3% $KH_2PO_4$, 0.05% NaCl, 0.1% $NH_4Cl$, 2 mM $MgSO_4$, 0.2% glucose and 0.1 mM $CaCl_2$) containing 50 µg/ml of ampicillin and 1% casamino acid and incubated at 37° C. with shaking. The cells were harvested when the absorbance (O.D.) at 550 nm reached 1.0 and suspended in 5 ml of a solution of 15% sucrose, 50 mM Tris HCl (pH 8.0) and 50 mM EDTA(pH 8.0). A 500 µl of 10 mg/ml lysozyme (as dissolved in 10 mM Tris HCl (pH 8.0)) was added to the suspension, and 5 ml of a solution of 0.3% Triton X100, 187.5 mM EDTA (pH 8.0) and 150 mM Tris HCl (pH 8.0) was further added to the mixture. The mixture was allowed to stand at room temperature for 15 minutes, then thoroughly stirred and centrifuged to obtain a supernatnat of cell extract having GIF activity.

(3) Purification and Identification of IL-1β Derivative

The above product was purified by chromatography in the same manner as in Preparation Example 1. The concentrated product thus obtained was checked for isoelectric point, amino acid composition and amino acid sequence to confirm that the product is the polypeptide having the amino acid sequence of the 24- to 153-position amino acids of the IL-1β represented by the formula (B).

PREPARATION EXAMPLE 6

Preparation of IL-1β Derivative (1-82)

(1) Preparation of Expression Plasmid

Plasmid ptrp GIF-α (Preparation Example 5) was digested with restriction enzyme PvuII, and then about 2.9 kbp of the DNA fragment which carries the region coding for the sequence of the 1- to 82-position amino acids of IL-1β was isolated by agarose gel electrophoresis.

XbaI linker (5'-CTCTAGAG-3') was 5' phosphorylated with T4 polynucleotide kinase. The linker was ligated with the above DNA fragment using T4 DNA ligase, followed by digestion with restriction enzymes ClaI and XbaI. The DNA fragment (250 bp) was thus isolated by agarose gel electrophoresis.

Plasmid pTM1 was digested with restriction enzyme BamHI and treated with DNA polymerase I (Klenow fragment) to convert the BamHI restriction site into blunt end. Using T4 DNA ligase, this DNA fragment was ligated with XbaI linker (5'-CTCTAGAG-3') 5'-phosphorylated with T4 polynucleotide kinase. The resulting product was then digested with restriction enzymes ClaI and XbaI. The DNA fragment carrying trp promoter, etc. was thus excised and isolated and purified by agarose gel electrophoresis.

This DNA fragment was ligated with 250 bp of the DNA fragment previously prepared using T4 DNA ligase, followed by transforming into E. coli HB101. The desired transformant was selected by restriction enzyme analysis of plasmid DNA obtained by the boiling method.

(2) Incubation of Transformant

The above transformant was incubated and treated in the same manner as in Preparation Example 5 to obtain a supernatant of cell extract having GIF activity.

(3) Purification and Identification of Il-1β Derivative The above product was purified in the same manner as in Preparation Example 5. The concentrated product thus obtained was checked for isoelectric point, amino acid composition and amino acid sequence to confirm that the product is the polypeptide having the amino acid sequence of the 1- to 82-position amino acids of the IL-1β represented by the formula (B).

EXAMPLE 1

Preparation of Medicament for Treating thrombocytopenia

To a saline solution of the polypeptide (IL1α.Δ(1-14).36D.141S) prepared in Preparation Example 2, which had GIF activity of $1\times10^6$ units/ml, human serum albumin (HSA) was added to a concentration of 0.5%. The mixture was filtrated with a membrane filter (0.22 µm), and 1 ml portions of the filtrate were aseptically placed into 1 ml-bials and lyophilized to give a pharmaceutical preparation for injection.

The preparation thus obtained was used as dissolved in 1 ml of distilled water.

EXAMPLE 2

Pharmacological Test I

The pharmacological effect of the active component of the inventive medicament for treating thrombocytopenia was evaluated in this example.

The polypeptides used as active components in the test were as follows:

IL-1α (36D.141S)

Derivative of IL-1α wherein Asn at the 36-position is replaced by Asp and Cys at the 141-position replaced by Ser (European Patent Publication No. 237073).

IL-1α (Δ(1-14).36D.141S)

Derivative of IL-1α (obtained in Preparation Example 2) wherein the sequence of the 1-position amino acid to the 14-position amino acid is deleted, and the 36-position Asn is replaced by Asp and the 141-position Cys by Ser.

IL-1α (16G.36D.141S)

Derivative of IL-1α (obtained in Preparation Example 1) wherein the 16-position Arg is replaced by Gly, the 36-position Asn by Asp, and the 141-position Cys by Ser.

IL-1β (native IL-1α)

Polypeptide having the amino acid sequence of the formula (β) (Biochem. Biophys. Res. Commun., 147(1), 315–321 (1987))

The test was performed using 9-week old male BALB/c mice (Experimental Animal Cooperation association of Shizuoka Prefecture, Japan)

Each of the above polypeptides (active components) was diluted to the prescribed concentration with a physiological saline for injection containing 100 µg/ml of mouse serum albumin (manufactured by Otsuka Pharmaceutical Factory, Inc.).

On the initial day (0 day), the animals were systemically irradiated with 400 Rad of X-ray using X-ray irradiation chamber for experimental small animals (Hitachi MBR-1505R) to induce thrombocytopenia.

From the following day, the test drug was subcutaneously administrated 13 times every day.

On the 14th day, the mice were anesthetized with ether. Blood was obtained from the inferior vena cava after laparotomy and collected in a microtainer (manufactured by Becton Dickinson). The blood cells were analysed using an automatic blood cell analyzer (ELT/8, Ortho Diagnostic System Inc.).

The experiment was done using 5 mice per group.

The number of platelets (mean±S.E.,×$10^3$/mm$^3$) on 14th day was shown below in Table 6.

TABLE 6

| Test Polypeptide | Dose (µg/kg) | | |
|---|---|---|---|
| | 0.1 | 1 | 10 |
| IL-1β | 1076 ± 41* | 1316 ± 54* | 1710 ± 47* |
| IL-1α [36D.141S] | 969 ± 40* | 1211 ± 32* | 1446 ± 37* |
| IL-1α [Δ(1–14).36D.141S] | 872 ± 17* | 1253 ± 15* | 1374 ± 69* |
| IL-1α [16.G.36D.141S] | 715 ± 23* | 911 ± 28* | 1220 ± 68* |
| Control Solvent Group | | 447 ± 52 | |
| Untreated normal Group | | 1164 ± 10 | |

The significant difference test was done according to Student's t-test employing the value of the solvent group as a control. In the above table * means $p \leq 0.001$.

As shown in Table 6, althogh the number of platelets was 1164±10 in the untreated normal group, the platelets decreased to 447±52 in the control group. On the other hand, in the present active component (IL-1 and its derivative) group, remarkable dose-dependent increase in platelete begun from at the dose of 0.1 µg/kg. The result indicates that the present active components are useful for therapy of thrombocytopenia.

EXAMPLE 3

Pharmacological Test II

The test was done in the same manner as in Pharmacological Test I using the IL-1α derivatives as follows:

IL-1α (native form)

IL-1α (36D.141S)

IL-1α (Δ(1-15))

Derivative of IL-1α wherein the sequence of the 1-position amino acid to the 15- position amino acid is deleted (obtained in Preparation Example 3).

IL-1α (Δ(1-15).36D)

Derivative of IL-1α wherein the sequence of the 1- to 15-position amino acids is deleted, and the 36-position Asn is replaced by Asp (obtained in Preparation Example 3).

IL-1α (Δ(1-15).36D.141S)

Derivative of IL-1α wherein the sequence of the 1- to 15-position amino acids is deleted, the 36-position Asn is replaced by Asp and the 141-position Cys by Ser (obtained in Preparation Example 4).

IL-1α (Δ(1-14).36D.141S)

Derivative of IL-1α wherein the sequence of the 1- to 14-position amino acids is deleted, the 36-position Asn is replaced by Asp and the 141-position Cys by Ser (obtained in Preparation Example 2).

The number of platelets (mean±S.E.,×$10^3$/mm$^3$) on the 14th day for each of the doses is shown below in Table 7, and the number of neutrophils (mean±S.E.,×$10^3$/mm$^3$) in Table 8.

TABLE 7

| Test Polypeptide | Dose (µg/kg) | | |
|---|---|---|---|
| | 0.1 | 1 | 10 |
| IL-1α | 794.0 ± 99.7* | 940.3 ± 80.7* | 1225.8 ± 55.5* |
| IL-1α [36D.141S] | 818.8 ± 13.2* | 1071.0 ± 36.0* | 1327.5 ± 28.8* |
| IL-1α [Δ(1–15)] | 778.0 ± 62.6* | 1077.3 ± 13.8* | 1347.5 ± 54.5* |
| IL-1α [Δ(1–15).36D] | 844.7 ± 56.6* | 932.3 ± 132.6* | 1218.8 ± 194.3* |
| IL-1α [Δ(1–15).36D.141S] | 862.7 ± 65.9* | 961.0 ± 12.1* | 1262.0 ± 4.4* |
| IL-1α | 637.8 ± 8.9* | 1022.5 ± 21.3* | 1158.0 ± 9.3* |

TABLE 7-continued

| | Dose (μg/kg) | | |
|---|---|---|---|
| Test Polypeptide | 0.1 | 1 | 10 |
| [Δ(1-14).36D.141S] | | | |
| Control Solvent Group | | 661.3 ± 33.2 | |
| Untreated normal Group | | 967.8 ± 13.1 | |

TABLE 8

| | Dose (μg/kg) | | |
|---|---|---|---|
| Test Polypeptide | 0.1 | 1 | 10 |
| IL-1α | 0.2 ± 0.0* | 1.7 ± 0.3* | 5.6 ± 1.0* |
| IL-1α [36D.141S] | 0.7 ± 0.1* | 2.3 ± 0.5* | 4.7 ± 0.5* |
| IL-1α [Δ(1-15)] | 0.1 ± 0.0* | 1.5 ± 0.0* | 4.1 ± 0.6* |
| IL-1α [Δ(1-15).36D] | 0.4 ± 0.1* | 1.5 ± 0.2* | 3.3 ± 1.2* |
| IL-1α [Δ(1-15).36D.141S] | 0.1 ± 0.1* | 0.8 ± 0.1* | 2.3 ± 0.4* |
| IL-1α [Δ(1-14).36D.141S] | 0.4 ± 0.0* | 1.4 ± 0.2* | 2.0 ± 0.5* |
| Control Solvent Group | | 1.4 ± 0.2 | |
| Untreated normal Group | | 0.0 ± 0.0 | |

EXAMPLE 4
Physiological Activity

The GIF acitivity of the IL-1α derivative is shown below in Table 9.

TABLE 9

| | GIF activity | |
|---|---|---|
| Test Polypeptide | Specific activity (U/mg) mean to S.D. | Relative activity |
| IL-1α | 8.90 ± 0.802 × 10⁶ | 1.00 |
| IL-1α [36D.141S] | 1.09 ± 0.0836 × 10⁷ | 1.22 |
| IL-1α [Δ(1-15)] | 1.86 ± 0.148 × 10⁶ | 0.21 |
| IL-1α [Δ(1-15).36D] | 2.42 ± 0.215 × 10⁶ | 0.27 |
| IL-1α [Δ(1-15).36D.141S] | 8.83 ± 0.526 × 10⁵ | 0.10 |
| IL-1α [Δ(1-14)36D.141S] | 6.97 ± 0.782 × 10⁵ | 0.08 |

EXAMPLE 5
Test of Pyrogenicity

The IL-1 and derivatives thereof were tested for pyrogenicity using rats as described below.

Male SD rats (6–10 week old, 160 to 250 g in body weight, Japan Charles River) were used in the experiment.

Each of the present derivatives and the other test substances for comparison was diluted to a specific concentration with phosphate saline buffer containing 100 μg/ml of rat serum albumin to give a test solution, and the dilution of human serum albumin (HSA) was employed as a control solution.

The prescribed amounts of the test solution and the control solution were given subcutaneously to the rats which were previously weighed. The rectal temperature of rat was determined using Thermister Temperature Recorder K923 (Takara Thermistor Instruments Co., Ltd.) before administration and 2, 4 and 6 hours after administration.

As test substances were used the present derivatives prepared in the preparation examples, comparative IL-1α (native form, Biochem. Biophys. Res. Commun., 147(1), 315–321 (1987)) and the comparative IL-1α derivative (the derivative of the formula (A) modified in that the 36-position Asn is replaced by Asp and the 141-position Cys by Ser, European Patent Publication No. 237073). The result (the rectal temperatures as measured 4 hours after administration when the temperature rises to a maximum) is shown in FIG. 1.

In FIG. 1, the dose (μg/kg) of test substance is plotted as abscissa and the change in rectal temperature (Δ° C.) from the temperature (0) immediately before administration is plotted as ordinate. Line (1) shows the result obtained by the present derivative of Preparation Example 1 (IL-1α.16G.141S), Line (2) shows the result obtained by the present derivative of Preparation Example 2 (IL-1α.Δ(1-14).36D.141S), Line (3) shows the result obtained by the native IL-1β, Line (4) shows the result obtained by the IL-1α derivative disclosed in the above European Patent Publication (IL-1α.36D.141S), and Line (5) shows the result obtained by the control (HSA).

FIG. 1 reveals that, since the derivative of the present invention does not substantially induce fever at all doses, thus exhibiting a remarkable inhibition of pyrogenicity. On the other hand, IL-1β induced fever at a dose of 0.1 μg/kg, and body temperature increased with a increase in dose. With IL-1α.36D.141S, although doses of 0.1, 1 and 10 μg/kg did not induce fever, a dose of 100 μg/kg induced fever.

The experiment was done in the same manner as above using the IL-1α derivatives prepared in Preparation Examples 3 and 4.

The result is shown in FIG. 2A and FIG. 2B. Lines (1) to (4) show the results obtained by the present derivatives: (1) by IL-1α(Δ(1-15)), (2) by IL-1α(Δ(1-15).36D), (3) by IL-1α(Δ(1-15).36D.141S) and (4) by IL-1α(Δ(1-14).36D.141S). Lines (5) to (8) show the results obtained by the comparative IL-1: (5) by IL-1α, (6) by IL-1α(36D), (7) by IL-1α(36D.141S) and (8) by [⁷¹Ser]-IL-1β (European Patent Publication No. 187991).

EXAMPLE 6
Hemopoietin-1 Activity Test

Hemopoietin-1 activity was determined by the method of Stanley, R. et al. (Cells, 45, 667–674, 1986). A 150 mg/kg quantity of 5-fluorouracil was given intravenously to a male BALB/c mouse (Cooperative Association of Shizuoka Prefecture Japan), and bone marrow cells (5-FU treated marrow cells) were isolated from femurs 3 day after administration. A specific concentration (200 U/ml) of mouse M-CSF and various concentrations of IL-1α or IL-1α derivative were added to the 1.5×10⁵ cells of the 5-FU treated marrow cells. The mixture was incubated in a soft agar medium, and the number of colonies formed on the culture medium was counted on the 7th day. The mouse M-CSF used was one prepared from L cell culture supernatant.

The result is shown below in Table 10.

TABLE 10

| | Hemopoietin Activity | |
|---|---|---|
| Test Polypeptide | ED₅₀ (ng/ml) | H-1 Activity |
| IL-1α | 0.1 | 10 |
| IL-1α (36D.141S) | 0.1 | 10 |
| IL-1α (Δ(1-15)) | 2.3 | 1 |
| IL-1α (Δ(1-15).36D) | 2.3 | 1 |
| IL-1α (Δ(1-15).36D.141S) | 2.3 | 1 |
| IL-1α (Δ(1-14).36D.141S) | 5 | 0.5 |

EXAMPLE 7

Clinical Test

To a 41-year-old female suffering from gastric cancer, in stage II with metastases to the liver, the lymph node, etc., 1×10⁴ GIF units of the IL-1β derivative of the formula (B) wherein the 71-position Cys is replaced by Ser was administrated subcutaneously once a day to test blood components.

As shown in Table 11, the number of platelets increased one week after administration and was after 3 weeks 1.7 times the value before the administration.

The number of white blood cells was increased to 1.8 times the number before the administration. The effect to diminish decreases in platelets and in white blood cells was not exhibited.

TABLE 11

|  | Before | 1 Week | 2 Weeks | 3 Weeks |
| --- | --- | --- | --- | --- |
| RBC (10⁴/mm³) | 377 | 359 | 374 | 352 |
| Hb (g/dl) | 10.8 | 10.2 | 10.8 | 10.2 |
| Ht (%) | 33.1 | 31.7 | 32.6 | 30.8 |
| Platelet (10⁴/mm³) | 14.9 | 16.4 | 21.2 | 25.8 |
| WBC (/mm³) | 5200 | 5300 | 9200 | 9300 |

We claim:

1. An IL-1α derivative having an amino acid sequence represented by the formula:

```
                5                      10
Ser—Ala—Pro—Phe—Ser—Phe—Leu—Ser—Asn—Val—
                15                     20
Lys—Tyr—Asn—Phe—Met—Arg—Ile—Ile—Lys—Tyr—
                25                     30
Glu—Phe—Ile—Leu—Asn—Asp—Ala—Leu—Asn—Gln—
                35                     40
Ser—Ile—Ile—Arg—Ala—X—Asp—Gln—Tyr—Leu—
                45                     50
Thr—Ala—Ala—Ala—Leu—His—Asn—Leu—Asp—Glu—
                55                     60
Ala—Val—Lys—Phe—Asp—Met—Gly—Ala—Tyr—Lys—
                65                     70
Ser—Ser—Lys—Asp—Asp—Ala—Lys—Ile—Thr—Val—
                75                     80
Ile—Leu—Arg—Ile—Ser—Lys—Thr—Gln—Leu—Tyr—
                85                     90
Val—Thr—Ala—Gln—Asp—Glu—Asp—Gln—Pro—Val—
                95                     100
Leu—Leu—Lys—Glu—Met—Pro—Glu—Ile—Pro—Lys—
                105                    110
Thr—Ile—Thr—Gly—Ser—Glu—Thr—Asn—Leu—Leu—
                115                    120
Phe—Phe—Trp—Glu—Thr—His—Gly—Thr—Lys—Asn—
                125                    130
Tyr—Phe—Thr—Ser—Val—Ala—His—Pro—Asn—Leu—
                135                    140
Phe—Ile—Ala—Thr—Lys—Gln—Asp—Tyr—Trp—Val—
                145                    150
J—Leu—Ala—Gly—Gly—Pro—Pro—Ser—Ile—Thr—
                155
Asp—Phe—Gln—Ile—Leu—Glu—Asn—Gln—Ala;
``` wherein each X and J is an amino acid residue commonly found in human proteins with the proviso that when X is Asn, J is not Cys; and wherein said derivative is IL-1α or IL-1α.

2. An IL-1α derivative having an amino acid sequence represented by the formula:

```
                5                      10
Ser—Ala—Pro—Phe—Ser—Phe—Leu—Ser—Asn—Val—
                15                     20
Lys—Tyr—Asn—Phe—Met—Arg—Ile—Ile—Lys—Tyr—
                25                     30
Glu—Tyr—Ile—Leu—Asn—Asp—Ala—Leu—Asn—Gln—
                35                     40
Ser—Ile—Ile—Arg—Ala—X—Asp—Gln—Tyr—Leu—
                45                     50
Thr—Ala—Ala—Ala—Leu—His—Asn—Leu—Asp—Glu—
                55                     60
Ala—Val—Lys—Phe—Asp—Met—Gly—Ala—Tyr—Lys—
                65                     70
Ser—Ser—Lys—Asp—Asp—Ala—Lys—Ile—Thr—Val—
                75                     80
Ile—Leu—Arg—Ile—Ser—Lys—Thr—Gln—Leu—Tyr—
                85                     90
Val—Thr—Ala—Gln—Asp—Glu—Asp—Gln—Pro—Val—
                95                     100
Leu—Leu—Lys—Glu—Met—Pro—Glu—Ile—Pro—Lys—
                105                    110
Thr—Ile—Thr—Gly—Ser—Glu—Thr—Asn—Leu—Leu—
                115                    120
Phe—Phe—Trp—Glu—Thr—His—Gly—Thr—Lys—Asn—
                125                    130
Tyr—Phe—Thr—Ser—Val—Ala—His—Pro—Asn—Leu—
                135                    140
Phe—Ile—Ala—Thr—Lys—Gln—Asp—Tyr—Trp—Val—
                145                    150
J—Leu—Ala—Gly—Gly—Pro—Pro—Ser—Ile—Thr—
                155
Asp—Phe—Gln—Ile—Leu—Glu—Asn—Gln—Ala;
``` wherein each of X and J is an amino acid residue commonly found in human proteins with the proviso that when X is Asn, J is not Cys; and wherein said derivative is IL-1α, IL-1α or IL-1α.

* * * * *